(12) United States Patent
Kwon

(10) Patent No.: US 6,934,031 B2
(45) Date of Patent: Aug. 23, 2005

(54) METHODS AND APPARATUS FOR DETERMINING OPTICAL CONSTANTS OF SEMICONDUCTORS AND DIELECTRICS WITH INTERBAND STATES

(75) Inventor: Daewon Kwon, Parsippany, NJ (US)

(73) Assignee: Rudolph Technologies, Inc., Flanders, NJ (US)

( * ) Notice: Subject to any disclaimer, the term of this patent is extended or adjusted under 35 U.S.C. 154(b) by 281 days.

(21) Appl. No.: 09/963,638

(22) Filed: Sep. 27, 2001

(65) Prior Publication Data

US 2003/0073254 A1 Apr. 17, 2003

(51) Int. Cl.$^7$ .................. G01N 21/55; G01N 21/41; G01N 4/00; H01L 21/66; B05D 5/06
(52) U.S. Cl. .................. 356/445; 356/128; 356/369; 438/16; 427/10
(58) Field of Search ................. 356/369, 630, 356/364, 445, 128; 250/225; 438/7, 14, 16; 427/8–10

(56) References Cited

U.S. PATENT DOCUMENTS

| | | | |
|---|---|---|---|
| 4,332,833 A | | 6/1982 | Aspnes et al. |
| 4,854,710 A | | 8/1989 | Opsal et al. |
| 5,883,518 A | | 3/1999 | Borden |
| 5,900,633 A | * | 5/1999 | Solomon et al. ....... 250/339.08 |
| 5,966,019 A | | 10/1999 | Borden |
| 5,999,267 A | * | 12/1999 | Zawaideh ................ 356/630 |
| 6,049,220 A | | 4/2000 | Borden et al. |
| 6,326,650 B1 | * | 12/2001 | Allam .................... 257/186 |
| 6,362,881 B1 | | 3/2002 | Pickering et al. |
| 6,392,756 B1 | * | 5/2002 | Li et al. ................ 356/632 |
| 6,563,578 B2 | * | 5/2003 | Halliyal et al. ......... 356/237.4 |

OTHER PUBLICATIONS

Tauc et al., "Optical Properties and Electronic Structure of Amorphous Germanium", *Phys. Stat. Sol.* 15, 627 (1966), pp. 627–637.

J. Bourgoin et al., *Point Defects in Semiconductors II*, Springer–Verlag, Berlin, Heidelberg, New York 1983.

"Modeling the Optical Dielectric Function of Semiconductors: Extension of the Critical–Point Parabolic–Band Approximation"; Kim, Physical Rev.B, vol. 45, No. 20, (May 1992).

"Parameterization of the Optical Functions of Amorphous Materials in the Interband Region", Jellison et al., Appl. Phys. Lett. 69(3) (Jul. 1996).

"Optical Dispersion Relations for Amorphous Semiconductor and Amorphous Dielectrics", Forouhi & Bloomer, Phys. Rev. B, vol. 34, No. 10, (Nov. 1986).

(Continued)

Primary Examiner—Zandra V. Smith
Assistant Examiner—Gordon J. Stock, Jr.
(74) Attorney, Agent, or Firm—Antonelli, Terry, Stout & Kraus, LLP

(57) ABSTRACT

A method for calculating the refractive index and the extinction coefficient for materials relates the physical parameters being calculated to the scattering caused by interband states in the material using a model which includes a quantum mechanical transition equation for transitions between valence and/or conduction bands and interband states of the material. The method can be used for material engineering, process control for processes affecting the interband states in the material, and in estimation of the amount of interband states which have been introduced into a material as a result of such a process. Apparatus for implementing the method are also disclosed.

20 Claims, 5 Drawing Sheets

OTHER PUBLICATIONS

"Optical Dispersion Relations for Si and Ge", Adachi, J. App. Phys. 66(7), (Oct. 1989).

From Optical Metrology, Overview of Variable Angle Spectroscopic Ellip[sometry (VASE), Part II, Johs et al., Soc. Photo–Opt. Instrum. Eng. (1999).

"Optical Propertues of Bulk and Thin–Film Sr–TiO2 on Si and PT", Zollner et al., J. Vac. Sci. Technol. B 19(4) (2000).

From Wiley Encyclopedia of Electrical and Electronics Engineering—Supplement 1, Editor Webster, John Wiley & Sons, (2000).

"Development of a Parametric Optical Constant Model for Hg10xCdxTe for Control of Composition by Spectroscopic Ellipsometry During MBE Growth", Johs et al., Thin Solid Films, 313–314 (1998).

* cited by examiner

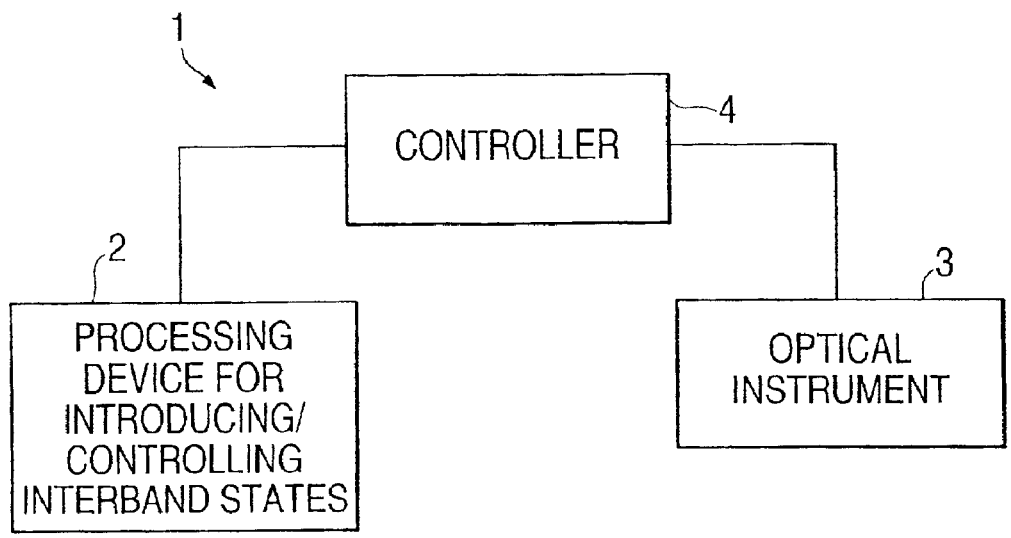
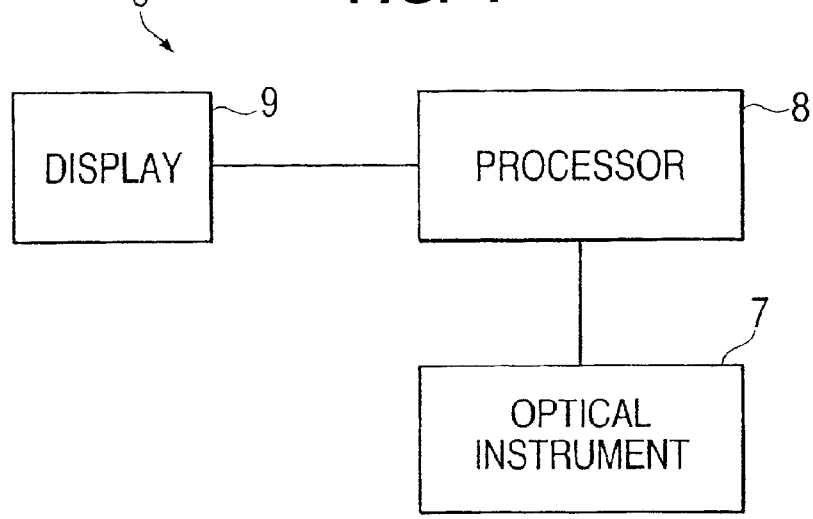

METHODS AND APPARATUS FOR DETERMINING OPTICAL CONSTANTS OF SEMICONDUCTORS AND DIELECTRICS WITH INTERBAND STATES

TECHNICAL FIELD

The present invention concerns a method of and apparatus for calculating at least one physical parameter of a film where the physical parameter is related to scattering caused by interband states. The relating is based upon a theoretical model including a quantum mechanical transition equation for transitions between a band and interband states. The equation contains parameters whose values for a given film are obtained from fitting measured data from an optical instrument such as a reflectometer and/or ellipsometer to the model. The model with fitted parameters enables calculation of the physical parameters. A value of one of the fitted parameters is proportional to the concentration of one interband state and, when calibrated against the magnitude of a variable of a process for introducing the interband state in the material, the parameter can be used for material engineering or monitored for process control. The invention is applicable, for example, to the manufacture of semiconductor or dielectric materials where alien species are introduced into the material as microscopic impurities which induce interband states.

BACKGROUND AND SUMMARY

Various schemes have been proposed for evaluating physical parameters of a semiconductor. In one example disclosed in U.S. Pat. No. 4,854,710, information is derived by analyzing the interaction between sample features and an electron-hole plasma induced in the sample. Variations in plasma density, which is in part a function of variations in the sample, are measured based on the effect of the plasma on the refractive index at the surface of the sample. A radiation probe is reflected off the surface of the sample and changes induced in the refractive index are monitored to obtain information about surface and subsurface characteristics of the sample.

The patentees in U.S. Pat. No. 4,854,710 state that their invention can be used for microscopically evaluating ion dopant concentrations in a semiconductor by measuring changes in reflectivity of a probe beam. A periodic energy beam is used to infuse energy into the sample and create an electron-hole plasma. The diffusion profile or changing density of the plasma is detected at the sample surface through the use of the probe beam. The changing output signals of the detected, reflected probe beam which are in phase with the energy beam can be plotted to indicate variations in dopant or defect concentrations. These output signals are compared to predetermined reflectivity measurements made on a known reference sample. The latter information can be stored in a processor and compared to give relative information concerning the tested sample.

U.S. Pat. No. 5,883,518 discloses a doping level measuring system which may be used to control a semiconductor fabrication process. In the measuring system a detector detects the phase shift of an analyzer beam relative to a reference beam, and the doping level in a preselected doped region is determined from the phase shift. The phase shift of an analyzer beam is also detected in a method disclosed in U.S. Pat. No. 5,966,019, which employs both an analyzer beam and a generation beam. A property of a semiconductor substrate is calculated from the detected phase shift.

U.S. Pat. No. 6,049,220 discloses an apparatus and method for evaluating a wafer of semiconductor material which use diffusive modulation (without generating a wave of carriers) for measuring a material property (such as any one or more of mobility, doping, and lifetime) that is used in evaluating a semiconductor wafer. The measurements are based on measurement of reflectance, for example, as a function of carrier concentration. In one implementation, the semiconductor wafer is illuminated with two beams, one with photon energy above the band gap energy of the semiconductor, and another with photon energy near or below the band gap. An attribute, derived from measurements on the wafer is interpolated with respect to corresponding attributes of wafers having a known material property (or process condition) to determine a corresponding property or condition of the wafer under measurement.

The Cauchy empirical model is the basis for modeling at least one physical parameter of a film for a wide variety of materials. Cauchy modeling can predict the experimental results in the long wavelength range where such optical transitions as band-to-band and band-to-interband state transitions do not occur. For example, Cauchy modeling can be used to fit the reflectance and ellipsometric measurement data of organic arc material for wavelengths longer than about 450 nm. However, data from measurements with light in the ultraviolet wavelength range do not match up well with the data predicted by the Cauchy model. There is a need for an improved model and method of calculating at least one parameter of a film using the model, which can accurately simulate or model the characteristic of a material for measurements over a wide range of wavelengths, including those in the ultraviolet wavelength range. An accurate model and method suitable for use with semiconductor materials and dielectrics having varying concentrations of interband states in the material would also be beneficial.

To this end, the improved method of the present invention for calculating at least one physical parameter of a film comprises relating at least one physical parameter to scattering caused by interband states. This relating includes using a theoretical model which includes a quantum mechanical transition equation for transitions between valence and/or conduction bands and interband states of the material. The method can be used for calculating the refractive index and the extinction coefficient of the film. It is applicable for semiconductor and dielectric film materials having varying levels of interband states. Apparatus for producing and monitoring films having at least one desired physical parameter, which employ the method are also provided.

These and other features and advantages of the present invention will become more apparent from the following description when taken in connection with the accompanying drawings which show, for purposes of illustration only, several example embodiments in accordance with the present invention.

BRIEF DESCRIPTION OF DRAWINGS

FIG. 3 is a schematic illustration of an embodiment of an apparatus for introducing or controlling interband states in a film according to a method of the present invention.

FIG. 4 is a schematic illustration of another embodiment of an apparatus for monitoring films according to the present invention.

DETAILED DESCRIPTION

The disclosed example embodiment of the present invention is a simulation method for calculating the refractive index n and the extinction coefficient k for film materials containing varying levels or concentrations of interband states. In the method, the physical parameters n and k of a film which are calculated are related to scattering caused by interband states. This is accomplished by modeling using a theoretical model which includes a quantum mechanical transition equation for transition between valence and/or conduction bands and interband states.

By way of explanation, it is known from equation (1) below from electromagnetic theory that $$\epsilon_2 = cn\alpha/\omega, \quad (1)$$

where
$\epsilon_2$ is the imaginary part of the dielectric function;
c is the speed of light;
n is the refractive index;
$\alpha$ is the absorption coefficient; and
$\omega$ is the angular frequency of light.

For the case of semiconductor or dielectric materials with interband states, it is known from equation (2) below that:

$$\alpha = N_T \sigma, \quad (2)$$

where
$N_T$ is the concentration of absorption centers per unit volume, such as per cm$^3$; and
$\sigma$ is the capture cross section of an absorption center.

Figure 2:
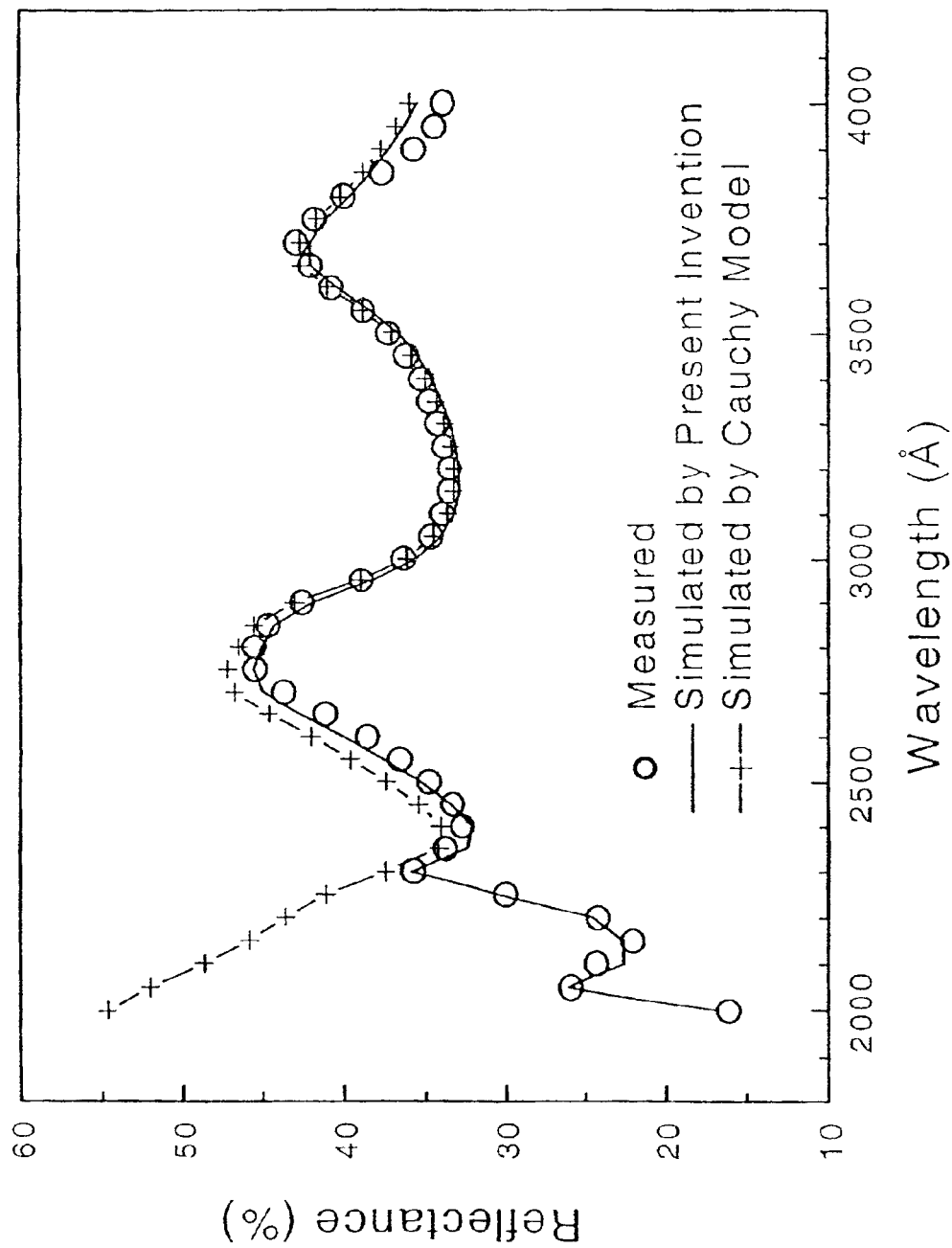
FIG. 2 is a graph showing the measured fitted results of reflectance of a film of organic anti-reflective coating (ARC) to incident light, wherein the three plots shown are one of measured data (shown by small circles) from the organic ARC material, a second plot (solid line) which is a simulation of the reflectance as a function of wavelength of the incident light for the same material from the model of the present invention, and a third plot (dashed line with cross hatching) which is a simulation based on the empirical Cauchy model.

The effect of interband states in a semiconductor or dielectric material on the optical properties, such as reflectance, of the material with varying wavelengths of incident light can be seen from the measured plot depicted in FIG. 2. The two sharp peaks in the reflectance, each followed by a sharp drop in reflectance, for light within the 2,000–2,500 Å wavelength are believed to be caused by the presence of interband states. These peaks do not occur in semiconductor or dielectric materials where interband states are absent.

Transparent, dielectric films are known to exhibit strong absorption bands. When the wavelength of the incident light approaches an absorption band of the material from the long-wavelength side, the refractive index of the material becomes very large, then decreases within the band to assume abnormally small values on the short-wavelength side, values below those for radiation on the long-wavelength side. The expression "normal variation" is used to describe the change in the refractive index of a material with changing wavelengths of light for wavelengths far removed from those of the absorption bands of the material. This variation can be expressed by Cauchy's formula. The expression "anomalous variation" refers to the very large increase and then decrease of the refractive index, or reflectance as shown in FIG. 2, as the wavelength approaches the absorption band from the long-wavelength side, then decreases within the band to assume abnormally small values on the short-wavelength side.

Figure 1:
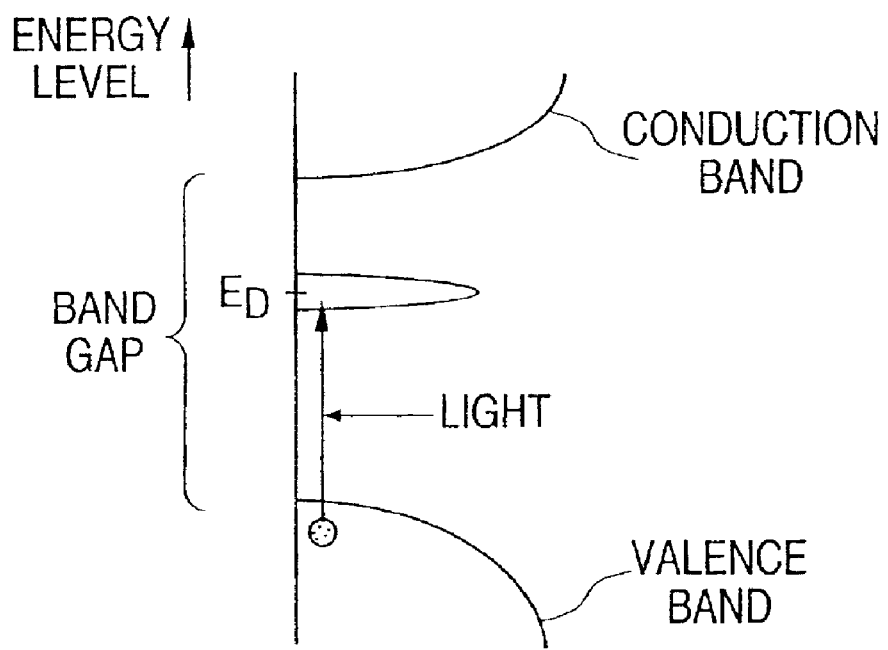
FIG. 1 is a schematic illustration of an optical transition between valence band and an interband state, causing a detectable drop in reflectance.

The method of the present invention is explained with reference to the schematic illustration in FIG. 1, wherein the band gap, close to 10 eV, for example, between the valence band and the conduction band is relatively large, higher than the energy level of the incident photons of the light used for the measurements of the material over the wavelength range shown in FIG. 2. To explain the anomalous variations, e.g., the sharp peaking and then decrease of the reflectance in the wavelength range 2,000–2,200 Å and the wavelength range 2,300–2,450 Å as shown in FIG. 2, interband states in the material which absorb energy in these wavelength ranges are considered to account for these abrupt changes. That is, the presence of the interband states permits absorption of energy by transition of electrons from the valence or conduction band to the interband state level, $E_D$.

A general quantum mechanical transition equation appears in equation (3) below. See J. Tauc et al.: "Optical Properties and Electronic Structure of Amorphous Germanium, *Phys. Stat. Sol.* 15, 627 (1966) at page 634.

$$\varepsilon_2(\omega) = \left(\frac{2\pi e}{m\omega}\right)^2 \frac{1}{V} \sum_{i,f} |P_{if}|^2 \delta(E_f - E_i - E), \quad (3)$$

where
$\epsilon_2(\omega)$ is the imaginary part of the dielectric function;
$P_{if}$ is the momentum matrix element between the wave functions of the final and initial states;
$E_f$ is the energy level of the final state;
$E_i$ is the energy level of the initial state;
E is the incident photon energy;
V is the volume;
m is electron mass; and
$\omega$ is the angular frequency of light.

Transition between an interband state and band, is described by the following derived equation (4). See J. Bourgoin et al.: *Point Defects in Semiconductors II Experimental Aspects*, Springer-Verlag Berlin Heidelberg New York 1983, page 110.

$$\varepsilon_2(\omega) = \begin{cases} A \dfrac{\sqrt{E - E_D}}{E^2}, & \text{for } E > E_D \\ 0, & \text{for } E < E_D \end{cases} \quad (4)$$

where A and $E_D$ are parameters which can be determined from fitting measured data from a film according to the model.

From the Kramer Konig relation, $\varepsilon_1(\omega)$ can be calculated from $\varepsilon_2$ according equation (5) as follows.

$$\varepsilon_1(\omega) = \varepsilon_1(\infty) + \frac{2}{\pi}\wp \int_0^\infty \frac{x\varepsilon_2}{x^2 - E^2} dx \qquad (5)$$

$$= \begin{cases} \varepsilon_1(\infty) + A\dfrac{2\sqrt{E_D} - \sqrt{E_D + E} - \sqrt{E_D - E}}{E^2}, & \text{for } E < E_D \\ \varepsilon_1(\infty) + A\dfrac{2\sqrt{E_D} - \sqrt{E_D + E}}{E^2}, & \text{for } E > E_D \end{cases}$$

where $\varepsilon_1(\omega)$ is the real part of the dielectric function; and $\varepsilon_1(\infty)$ is the value of $\varepsilon_1(\omega)$ at infinite angular frequency. This is a fitted parameter for the material obtained from measured data.

According to the invention, the parameters for fitting ellipsometric and reflectivity data using the model of the invention are thickness, $\varepsilon_1(\infty)$, and two additional parameters per defect level (A and $E_D$). Therefore, the maximum number of parameters will be 2+2 times the number of interband state levels present. Solving for the fitting parameters from measurements from a given material allows one to calculate $\varepsilon_1$ and $\varepsilon_2$ from which n and k can be calculated according to the following relations (6) and (7):

$$n = \sqrt{\frac{1}{2}\left[\sqrt{\left(\frac{\varepsilon_1}{\varepsilon_2}\right)^2 + \left(\frac{\varepsilon_2}{\varepsilon_0}\right)^2} + \frac{\varepsilon_2}{\varepsilon_0}\right]} \qquad (6)$$

$$k = \sqrt{\frac{1}{2}\left[\sqrt{\left(\frac{\varepsilon_1}{\varepsilon_0}\right)^2 + \left(\frac{\varepsilon_2}{\varepsilon_0}\right)^2} + \frac{\varepsilon_1}{\varepsilon_0}\right]} \qquad (7)$$

The fitted parameter A in the above equations depends on the concentration of the interband state as it is implemented in equation (2). In a thin film semiconductor and dielectric manufacturing facility or FAB environment, the concentration of interband state is controlled by, for example, adjusting the concentration of alien species introduced into a host material or by adjusting film preparation conditions. For example, alien species will be introduced in gas phase in a reactive chamber and the amount of gas flow is the controllable variable. Thus, according to the invention, the parameter A can be monitored, either during or after a process for introducing alien species into the material, to monitor whether there is a problem of controlling the concentration of alien species being used in the production process.

More generally, the application of the method and model of the invention enable material engineering by calibrating the concentration of alien species against the fitted parameter A, calculating refractive index and extinction coefficient (n and k) for the corresponding A, and deciding the concentration of alien species for the desired refractive index n and extinction coefficient k. Process control can be achieved by monitoring the fitted parameter A to monitor whether there is a problem of controlling the concentration of alien species, as noted above. An estimation of alien species in a film can also be obtained from the fitted parameter A.

The simulated plot in FIG. 2, obtained using the measured data from an organic ARC film and the model of the invention, validates the theoretical model of the present invention in closely following the measured data for reflectance as a function of the wavelength of the incident light. The other plot in FIG. 2 was obtained from the empirical Cauchy formula. As seen in FIG. 2, the plot from the Cauchy formula is not accurate in the wavelength range illustrated in FIG. 2 because it does not account for changes due to the presence of interband states in the material.

An apparatus 1 depicted in FIG. 3 according to the invention for producing a film having at least one desired physical parameter comprises a processing device 2 for introducing or controlling interband states in a film which affect the optical dispersion of the film. For example, an impurity can be carried by gas for diffusion into a material in the device 2 as will be understood by the skilled artisan. Other process variables which could be controlled include the temperature and/or time of treatment of the film being processed. An optical instrument 3, such as a reflectometer or ellipsometer, is provided for producing measured data from a film, either in situ in the device 2 during process or after production of the film with interband states.

A controller 4 of the apparatus adjusts a concentration of alien species being introduced in a film by the processing device 2 or adjusts another process variable, such as time and/or temperature of a treatment performed by the processing device causing interband states. Illustratively, the amount of gas flow containing the alien species to be introduced into a material can be adjusted by the controller for obtaining a material having the desired properties. The controller 4 receives measured data from the optical instrument 3. The controller can be a programmed processor such as a microprocessor that calculates a physical parameter or parameters of the measured film using the measured data and the theoretical model of the invention relating the physical parameter to scattering caused by film interband states in the material as discussed above.

An apparatus 6 of the invention depicted in FIG. 4 comprises an optical instrument 7 for measuring a film in which an alien species has been introduced or a film otherwise treated to have varying concentrations of interband states and for producing measured data as a result of the film measuring. The device 7 can be a reflectometer and/or ellipsometer, for example. A programmed processor 8 calculates at least one physical parameter of the measured film and displays it at display 9 using the measured data and the theoretical model according to the invention relating the physical parameter to scattering caused by interband states in the film. From initial measured data of a sample, the fitting parameters of the model can be calculated for use in calculating n and k and the fitted parameter A can be monitored for the aforesaid purposes.

Figure 5:
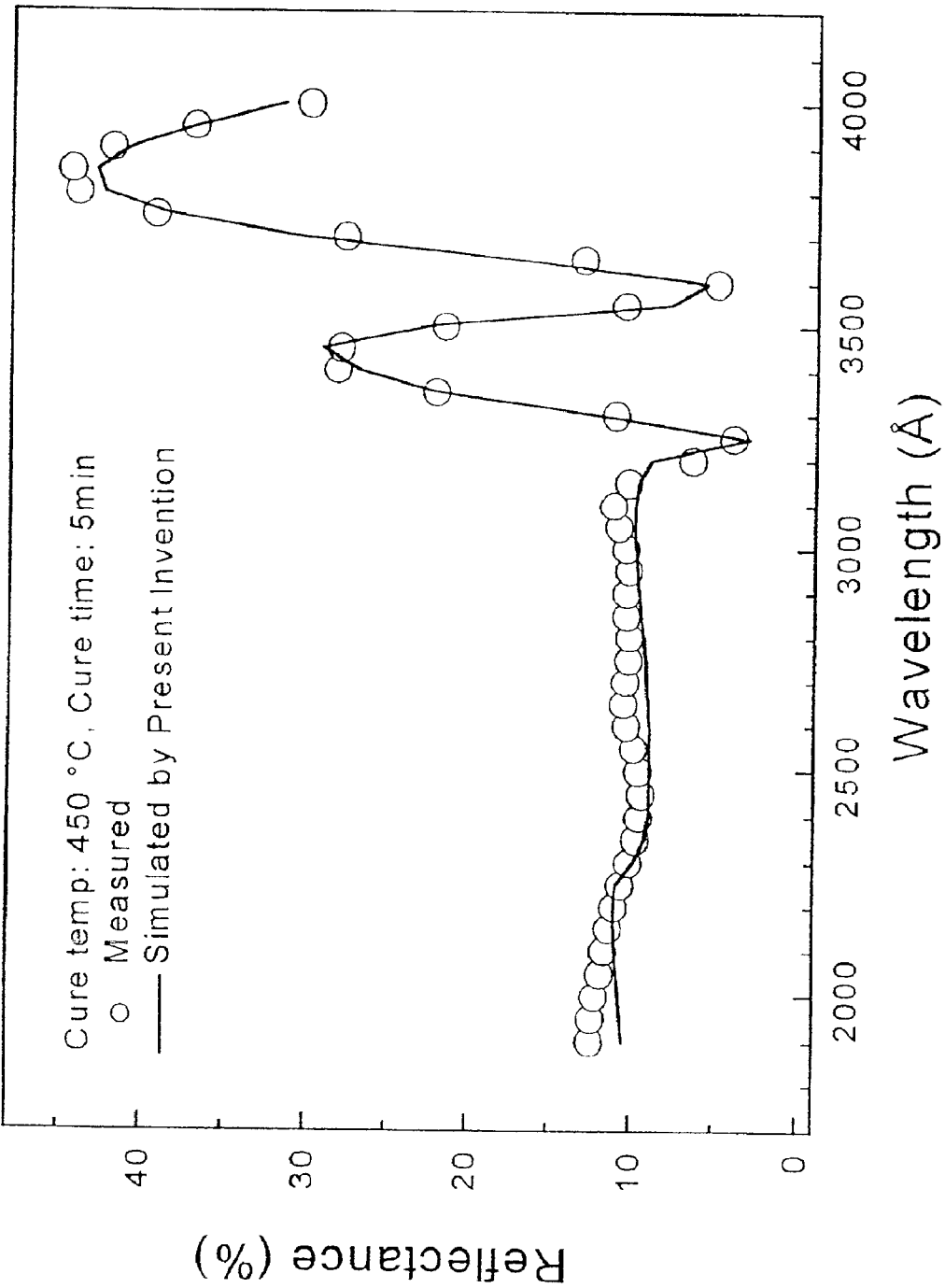
FIG. 5 is a graph showing the measured fitted results of reflectance of a film of a polymeric low k dielectric material which has been cured at a temperature of 450° C. for a curing time of 5 minutes, wherein the two plots shown are one of measured data (shown by small circles) from the silicon material, and the second plot (solid line) is a simulation of the reflectance as a function of wavelength of the incident light for the same material from the model of the present invention.

FIG. 5 shows the measured fitted results according to the present invention of reflectance of a film of a polymeric low k dielectric material by Dow Chemical Company. The film was processed by a process which caused varying concentrations of interband states. The concentration or level of interband states in the processed film was, at least in part, a function of both a curing temperature and also a cure time of the process. The two plots shown in FIG. 5 are each reflectance as a function of wavelength of the incident light on the material, one from measured data (shown by small circles) from the polymeric low k dielectric material, and the second plot (solid line) from a simulation from the model of the present invention. The measured fitted results in FIG. 5 are for film cured at a temperature of 450° C. for a cure time of 5 minutes. The simulated plot in FIG. 5 is seen to closely follow the measured data, further validating the model of the invention.

Figure 6:
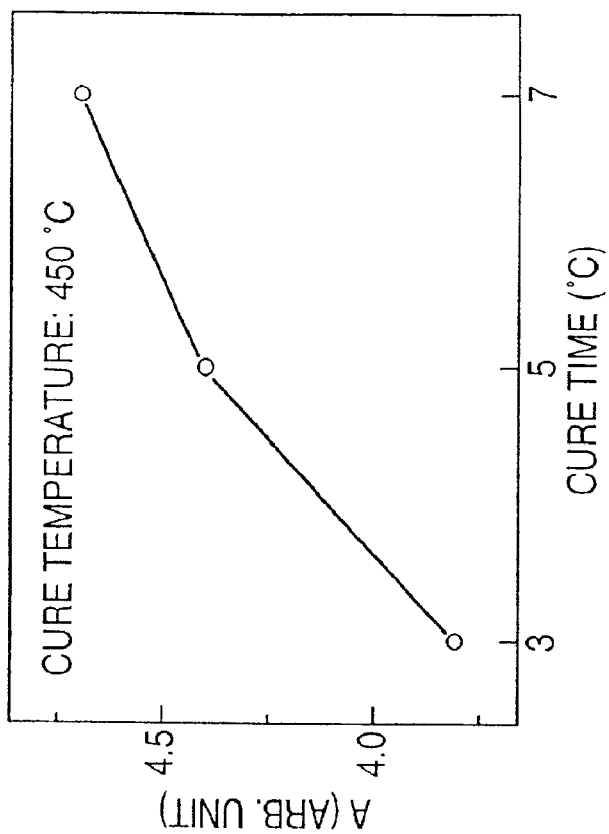
FIG. 6 is a graph showing the fitted parameter A of the model of the invention as a function of the cure temperature, with a curing time of 5 minutes, for the film of polymeric low k dielectric material.
Figure 7:
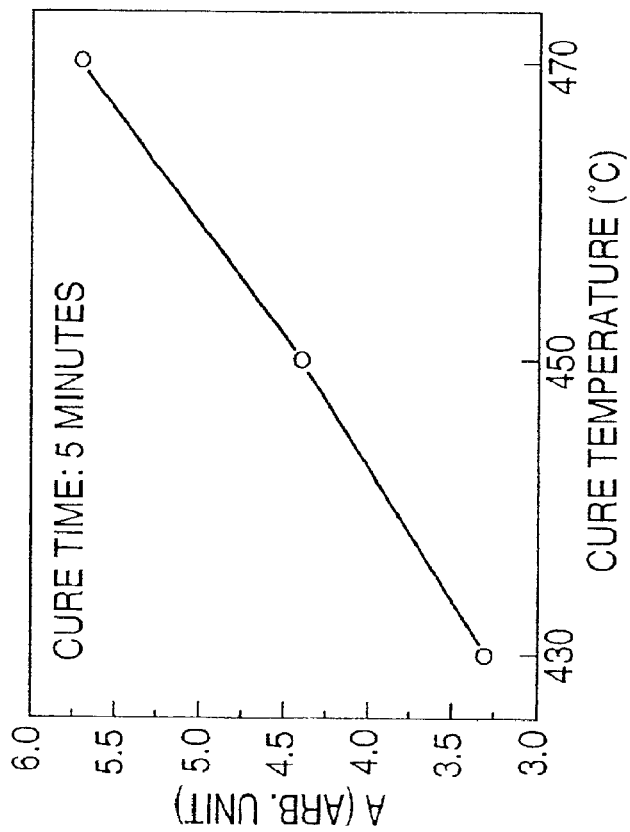
FIG. 7 is a graph showing the fitted parameter A of the model of the invention as a function of the cure time, with a cure temperature of 450° C., for the film of polymeric low k dielectric material.

FIGS. 6 and 7 are graphs of the fitted parameter A of the model of the present invention as a function of the cure temperature, FIG. 6, with a cure time of 5 minutes, for the film of polymeric low k dielectric material, and as a function of the cure time, FIG. 7, with a cure temperature of 450° C., for the film. Values for the fitted parameter A as a function of cure temperature and cure time for the film material having three levels of interband states, A1, A2 and A3, are shown in Table I below. The values for the fitted parameter A for the material with concentration A2 of interband states are shown as a function of cure temperature and cure time in FIGS. 6 and 7, respectively.

TABLE I

| Cure Temperature (° C.) | Cure time (minutes) | A1 | A2 | A3 |
|---|---|---|---|---|
| 430 | 5 | 19.97 | 3.317 | 0.802 |
| 560 | 3 | 18.37 | 4.398 | 1.051 |
| 450 | 5 | 19.09 | 3.806 | 0.944 |
| 450 | 7 | 17.76 | 4.690 | 1.124 |
| 470 | 5 | 16.49 | 5.674 | 1.312 |

While I have shown and described only several embodiments in accordance with the present invention, it is understood that the same is not limited thereto, but is susceptible to numerous changes and modifications as known to those skilled in the art. For example, although the method and apparatus of the invention have been explained in connection with calculating physical parameters, and material engineering, of materials where interband states are caused by introduction of alien species into the material, the method and apparatus are useful with materials, and in processes wherein interband states are caused by other mechanisms, such as by dislocations or coordination, e.g., bonding defects in the material. Therefore, I do not wish to be limited to the details shown and described herein, but intend to cover all such changes and modifications as are encompassed by the scope of the following claims.

I claim:

1. A method of calculating at least one physical parameter of a film in which the improvement comprises using a model for relating the at least one physical parameter to scattering caused by interband states, wherein the model is indicative of characteristic of the film over a wide range of wavelengths including in the UV wavelength range, the model taking into account transitions between a band and interband states in a band gap of the film.

2. The method according to claim 1, wherein the at least one physical parameter is an optical property of the film.

3. The method according to claim 1, wherein the at least one physical parameter is selected from the group consisting of the optical dispersion, refractive index and the extinction coefficient of the film.

4. The method according to claim 1, wherein both the refractive index and the extinction coefficient of the film are calculated.

5. The method according to claim 1, wherein the model includes a quantum mechanical transition equation for transitions between at least one of valence and conduction bands and interband states in a band gap.

6. The method according to claim 5, wherein the equation is:

$$\varepsilon_2(\omega) = \begin{cases} A\dfrac{\sqrt{E-E_D}}{E^2}, & \text{for } E > E_D \\ 0, & \text{for } E < E_D \end{cases}$$

where $\varepsilon_2(\omega)$ is the imaginary part of the dielectric function;
E is the incident photon energy;
$E_D$ is the energy level of the interband state; and wherein the values for A and $E_D$ are fitted parameters obtained from measured data of an optical property of the film.

7. The method according to claim 6, wherein the model further includes the equation:

$$\varepsilon_1(\omega) = \begin{cases} \varepsilon_1(\infty) + A\dfrac{2\sqrt{E_D} - \sqrt{E_D+E} - \sqrt{E_D-E}}{E^2}, & \text{for } E < E_D \\ \varepsilon_1(\infty) + A\dfrac{2\sqrt{E_D} - \sqrt{E_D+E}}{E^2}, & \text{for } E > E_D \end{cases}$$

where $\varepsilon_1(\omega)$ is the real part of the dielectric function;
$\varepsilon_1(\infty)$ is the value of $\varepsilon_1(\omega)$ at infinite angular frequency; and
wherein $\varepsilon_1(\infty)$ is a fitted parameter obtained from measured data of an optical property of the film.

8. The method according to claim 7, including using the values for $\varepsilon_1(\omega)$ and $\varepsilon_2(\omega)$ obtained by the modeling to calculate the physical parameters refractive index n and extinction coefficient k of the film according to the relations:

$$n = \sqrt{\dfrac{1}{2}\left[\sqrt{\left(\dfrac{\varepsilon_1}{\varepsilon_2}\right)^2 + \left(\dfrac{\varepsilon_2}{\varepsilon_0}\right)^2} + \dfrac{\varepsilon_2}{\varepsilon_0}\right]}$$

$$k = \sqrt{\dfrac{1}{2}\left[\sqrt{\left(\dfrac{\varepsilon_1}{\varepsilon_0}\right)^2 + \left(\dfrac{\varepsilon_2}{\varepsilon_0}\right)^2} + \dfrac{\varepsilon_1}{\varepsilon_0}\right]}.$$

9. The method according to claim 6, wherein the measured data of an optical property of the film for obtaining the fitted parameters are from a reflectometer and/or an ellipsometer.

10. The method according to claim 1, wherein the film is a semiconductor material containing at least one alien species as an impurity forming interband states in the semiconductor material.

11. The method according to claim 1, wherein the film is selected from the group consisting of a semiconductor material and a dielectric material.

12. An apparatus comprising:
an optical instrument for measuring an optical property of a film containing interband states and producing measured data as a result of the film measuring; and
a programmed computer for calculating at least one physical parameter of the measured film using the measured data and a theoretical model relating the physical parameter to scattering caused by interband states, wherein the model is indicative of characteristic of the film over a wide range of wavelengths including in the UV wavelength range, the model taking into account transitions between a band and interband states in a band gap of the film.

13. The apparatus according to claim 12, wherein the optical instrument is selected from the group consisting of a reflectometer and an ellipsometer.

14. The apparatus according to claim 12, wherein the at least one physical parameter is selected from the group consisting of the optical dispersion, refractive index and the extinction coefficient of the film.

15. The apparatus according to claim 12, wherein both the refractive index and the extinction coefficient of the film are calculated.

16. An apparatus comprising:
first means for measuring a physical property of a film containing interband states and producing measured data as a result of the film measuring; and second means for calculating at least one physical parameter of the measured film using the measured data and a model relating the at least one physical parameter to scattering caused by interband states, wherein the model is indicative of characteristic of the film over a wide range of wavelengths including in the UV wavelength range, the model taking into account transitions between a band and interband states in a band gap of the film.

17. A machine-readable medium containing at least one sequence of instructions that, when executed, causes a machine to:

calculate at least one physical parameter of a film containing interband states, using measured data of a physical property of the film and a model relating the at least one physical parameter to scattering caused by interband states, wherein the model is indicative of characteristic of the film over a wide range of wavelengths including in the UV wavelength range, the model taking into account transitions between a band and interband states in a band gap of the film.

18. The machine-readable medium according to claim 17, wherein the physical property measured is an optical property.

19. The machine-readable medium according to claim 17, wherein the at least one physical parameter is selected from the group consisting of the optical dispersion, refractive index and the extinction coefficient of the film.

20. The machine-readable medium according to claim 17, wherein both the refractive index and the extinction coefficient of the film are calculated.

* * * * *